US012617764B2

(12) United States Patent (10) Patent No.: US 12,617,764 B2
Lu et al. (45) Date of Patent: May 5, 2026

(54) DIHYDROMYRICETIN EXTRACTION AND PURIFICATION PROCESS

(71) Applicant: Dr Kang International Limited, Hongkong (CN)

(72) Inventors: Xinxin Lu, Ankang (CN); Likang Chen, Ankang (CN); Yukang Zhang, Ankang (CN)

(73) Assignee: Dr Kang International Limited, Hongkong (CN)

( * ) Notice: Subject to any disclaimer, the term of this patent is extended or adjusted under 35 U.S.C. 154(b) by 358 days.

(21) Appl. No.: 18/431,312

(22) Filed: Feb. 2, 2024

(65) Prior Publication Data

US 2025/0250247 A1     Aug. 7, 2025

(51) Int. Cl.
| | |
|---|---|
| *C07D 311/32* | (2006.01) |
| *B01D 9/00* | (2006.01) |
| *B01D 11/02* | (2006.01) |
| *B01D 21/00* | (2006.01) |
| *B01D 37/00* | (2006.01) |
| *C07D 311/40* | (2006.01) |
| *C07D 311/64* | (2006.01) |

(52) U.S. Cl.
CPC .......... *C07D 311/64* (2013.01); *B01D 9/0004* (2013.01); *B01D 11/0288* (2013.01); *B01D 11/0296* (2013.01); *B01D 21/0027* (2013.01); *B01D 37/00* (2013.01); *B01D 2009/0086* (2013.01)

(58) Field of Classification Search
CPC .. C07D 311/32; C07D 311/40; B01D 9/0004; B01D 9/0013; B01D 9/0054; B01D 9/0059; B01D 2009/0086; B01D 11/028; B01D 11/0288; B01D 11/0296; B01D 21/0027; B01D 37/00
See application file for complete search history.

(56) References Cited

FOREIGN PATENT DOCUMENTS

| | | |
|---|---|---|
| CN | 112715939 A | 4/2021 |
| CN | 114163411 A | 3/2022 |
| CN | 116036021 A | 5/2023 |

*Primary Examiner* — Brenda L Coleman
(74) *Attorney, Agent, or Firm* — Nitin Kaushik

(57) ABSTRACT

The present invention relates to the field of dihydromyricetin extraction and purification, and in particular to a dihydromyricetin extraction and purification process. Technical problem: the dihydromyricetin extraction and purification process aims to resolve the technical problems of increased cost of subsequent impurity removing and safety risks in high-temperature centrifugation in the prior art. Technical solution: a dihydromyricetin extraction and purification process: step 1: weighing a raw material, adding an extraction solvent in an amount 5 times that of the raw material to perform reflux extraction, concentrating the filtrate to an extract, and recovering acetone; step 2: resting for crystallization for 24 hours; step 3: performing suction filtration to obtain light-green sediment underneath, and dry the sediment; step 4: adding 5%-10% activated carbon for decolorization and impurity removing; step 5: performing suction filtration; step 6: drying to obtain white powder of dihydromyricetin; and step 7: detecting a content with HPLC.

9 Claims, 1 Drawing Sheet

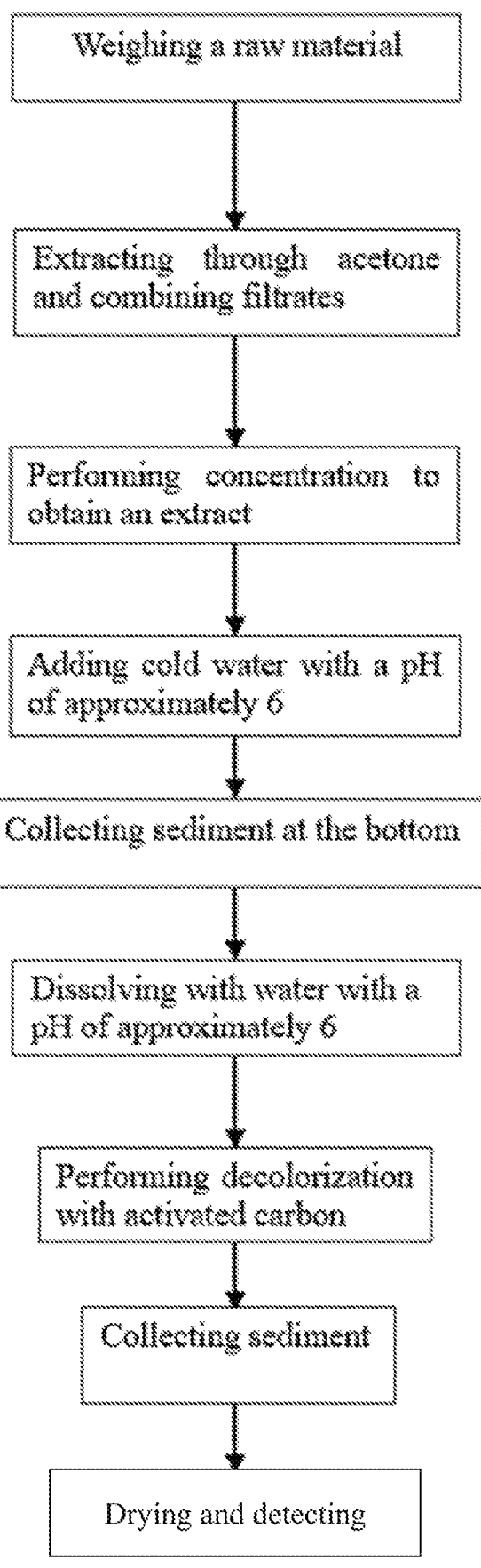

DIHYDROMYRICETIN EXTRACTION AND PURIFICATION PROCESS

TECHNICAL FIELD

The present invention relates to the field of dihydromyricetin extraction and purification, and in particular to a dihydromyricetin extraction and purification process.

BACKGROUND

Dihydromyricetin is a special flavonoid compound having a variety of unique effects such as scavenging free radicals, an antioxidant effect, an antithrombotic effect, an anti-tumor effect, and an anti-inflammatory effect as well as the functions such as relieving alcoholism, preventing alcoholic liver disease and fatty liver disease, inhibiting deterioration of liver cells, and reducing the incidence of liver cancer, and it is a good choice for protecting liver and sobering up. There are many dihydromyricetin extraction and purification methods according to literature, for example, a hot water extraction method, an ultrasonic-assisted extraction method, and a microwave extraction method, etc. However, these methods have problems of poor subsequent decolorization and high costs for mass production with ultrasonic wave.

As the domestic and foreign manufacturers keep the processes of optimization of dihydromyricetin extraction strictly confidential, there are just a few patents that have been granted.

A method for separating and purifying myricetin and dihydromyricetin from *Ampelopsis grossedentata* is disclosed in the Chinese patent (CN201610621955.8) filed by Hunan Nutramax Inc. on Jul. 29, 2016. The scope of protection for the claims of the method comprises the following steps:

step 1: preparation: weighing, selecting and crushing *Ampelopsis grossedentata* and then sieving it with a 35-45 mesh sieve; step 2: extraction: adding 75%-85% alcohol at a weight 18-22 times that of the *Ampelopsis grossedentata*, adding a 5% sodium bicarbonate solution to adjust the pH value to 7.0-8.0, soaking for 6-10 hours, and then performing reflux extraction at a temperature of 35-45° C. for 3-5 hours; step 3: secondary extraction: adding 75%-85% alcohol at a weight 8-12 times that of the *Ampelopsis grossedentata*, and performing reflux extraction at a temperature of 35-45° C. for 3-5 hours; step 4: filtration: combining liquid from the two times of extraction and performing filtration to obtain a filtrate; step 5: alcohol recovery: recovering alcohol from the filtrate until the alcohol concentration is 15% or below, and then performing vacuum concentration to obtain an extract having a specific gravity of 1.0-1.5; step 6: water sedimentation: mixing the concentrated extract thoroughly with hot water of 90-98° C. at a weight 18-22 times that of the concentrated extract and performing ultrasonic oscillation for 2.5-35 hours, performing high-speed centrifugation at a temperature of 80-90° C., and collecting a supernatant; step 7: centrifugation: refrigerating the supernatant obtained in step 6 overnight, performing high-speed centrifugation the next day, collecting a sediment, and performing vacuum drying to obtain the initial yellow-green extract powder; step 8: separation and purification: separating and purifying the initial extract obtained in step 7 to obtain myricetin and dihydromyricetin pure products having a high purity of 98% or above.

A process for extracting myricetin and dihydromyricetin is disclosed in the Chinese patent (CN105037310A) filed by Liuzhou Lvxiang Biotechnology Co., Ltd. on Jun. 5, 2015. The scope of protection for the claims of the method comprises the following steps: with *Ampelopsis grossedentata* as a raw material, the specific steps are as follows: 1) triple extractions: adding a fresh raw material of 500 g of leaves of *Ampelopsis grossedentata* into 3 L of 60% ethanol, stirring, and cold soaking for 2 hours, performing filtration with 100-mesh filter cloth, and then collecting a filtrate; adding 3 L of 60% ethanol to the filter residue, stirring, and cold soaking for 2 hours, performing filtration with 100-mesh filter cloth, and then collecting a filtrate; and adding 1 L of 60% ethanol and 150 g of vitamin C to the filter residue after the second extraction, stirring, and cold soaking for 1 hour, performing filtration with 100-mesh filter cloth, and collecting a filtrate; 2) clarification: combining the three filtrates collected in step 1), adding 1 ml of a clarifying agent, stirring well and resting, and then performing filtration on the clarified liquid with a suction filtration tank in which 3 g of diatomaceous earth is spread as a filter aid; 3) decolorization and filtration: adding 10 g of activated carbon and 2 g of vitamin C, heating up to 60 Celsius degrees and maintaining the temperature, stirring for 20 minutes, and then performing liquid drainage for filtration; 4) crude crystal formation: cooling the filtrate for crystallization, and performing crystal suction filtration to obtain 180 g of dihydromyricetin crude crystal having a content of 80%; 5) refining: heating 540 ml of 30% ethanol to 62 Celsius degrees, adding vitamin C in an amount 1.5 times that of the crude crystal first, then adding the crude crystal, stirring, after dissolving thoroughly, adding 3.6 g of activated carbon, stirring for 20 minutes, filtering the decolorized solution, resting the filtrate for 24 hours, and filtering the crystallized solution to obtain 130 g of dihydromyricetin having a content of 98%; and then recovering 270 ml of alcohol from the crystallized mother solution, adjusting the pH to 5 by using sodium bicarbonate, resting at room temperature for 24 hours, and filtering the crystallized solution to obtain 10 g of myricetin having a content of 95%.

Although the foregoing methods can obtain high-content refined dihydromyricetin products, there are challenges in controlling centrifugation at a high temperature and high speed, and achieving industrialization with ultrasonic oscillation which requires complex processes and high material cost. The ultrasonic oscillation faces the following problems: other flavonoids are prone to be introduced after ultrasonic oscillation, which increases the cost of subsequent impurity removing; while high-temperature and high-speed centrifugation faces the following problems: dihydromyricetin has a high solubility in hot water and is almost insoluble in water of low temperature, therefore, temperature control is needed during centrifugation, moreover, high-temperature centrifugation poses safety risks, and the extraction process involves the use of materials such as diatomaceous earth and vitamin C, and thus the cost of extraction is increased. Therefore, the foregoing methods face certain challenges in industrial production and have high production costs.

SUMMARY

In view of the drawbacks in the prior art, the objective of the present invention is to provide a dihydromyricetin extraction and purification process, which aims to resolve the technical problems of increased cost of subsequent impurity removing and safety risks in high-temperature centrifugation in the prior art.

The technical solution of the present invention is as follows: a dihydromyricetin extraction and purification process, comprising the following steps:

step 1: weighing a raw material, adding an extraction solvent in an amount 5 times that of the raw material to perform reflux extraction, after performing three times of extraction and filtering of extraction solutions, combining filtrates from the three times of extraction, concentrating the filtrate to an extract, and recovering acetone;

step 2: adding water to the extract in proportion and resting for crystallization for 24 hours;

step 3: skimming off black oily substance floating on the surface, performing suction filtration to obtain light-green sediment underneath, and drying the sediment;

step 4: heating and dissolving the crude product in pure water, and after thorough dissolution, adding 5%-10% activated carbon for decolorization and impurity removing;

step 5: performing suction filtration, and cooling the mother solution and resting for crystallization;

step 6: after the mother solution being cooled, performing suction filtration to obtain crystal, and drying the crystal so as to obtain white powder of dihydromyricetin; and step 7: detecting a content with HPLC.

Preferably, the raw material is dry leaves of *Ampelopsis grossedentata*, produced in Zhangjiajie, Hunan Province, China, with an amount of 0.1 kg to 10 kg.

Preferably, the extraction solvent is acetone.

Preferably, the temperature for the reflux extraction in step 1 is 60° C. and the extraction time is 50 minutes.

Preferably, the water in step 2 has a pH of 6±0.1 at room temperature.

Preferably, the volume ratio of the extract to the water in step 2 is 1:7.

Preferably, the pure water in step 4 has a pH of less than 7.

Preferably, the amount of the pure water used in step 4 is 18-20 times that of the crude product.

Preferably, the mother solution in step 6 is cooled to room temperature or below 15° C.

The beneficial effects of the present invention: the product has a short production cycle, allowing it to meet market demands within a short period of time; acetone is a solvent with the highest solubility for chlorophyll among commonly-used solvents, and acetone can be used to efficiently extract chlorophyll at room temperature through oscillation without the need for heating, in addition, acetone is cost-effective compared to other solvents; the extraction process consumes less energy, and fewer raw materials are used in the purification process, avoiding the introduction of other impurities and waste of raw materials, thereby reducing costs; water is used as a solvent for subsequent purification, which facilitates crystallization in a better way as compared to ethanol, is closer to standard in color, and makes decolorization easier, thereby not only saving costs but also reducing the solubility of other flavonoids and relieving challenges in subsequent impurity removing and decolorization; with the method of the present invention, the content of the product by HPLC detection is over 96%, and a high comprehensive utilization is realized, avoiding waste of raw materials; by using acetone for extraction, water for recrystallization, and activated carbon for decolorization, dihydromyricetin with a high content can be produced, and the extraction rate is high; moreover, this process is time-efficient, easy to operate, cost-effective, and suitable for industrial production.

BRIEF DESCRIPTION OF DRAWINGS

The FIGURE shows a flowchart of a dihydromyricetin extraction and purification process of the present invention.

DETAILED DESCRIPTION OF THE EMBODIMENTS

The present invention will be further described in conjunction with the accompanying drawings and embodiments.

Embodiment 1

Referring to the FIGURE the present invention provides an embodiment: a dihydromyricetin extraction and purification process, comprising the following steps:

step 1: weighing a raw material of 0.1 kg of dry leaves of *Ampelopsis grossedentata* produced in Zhangjiajie, Hunan Province, China, adding an extraction solvent in an amount 5 times that of the raw material to perform reflux extraction at 60° C. for 50 minutes, where the extraction solvent is acetone, after performing three times of extraction and filtering of extraction solutions, combining filtrates from the three times of extraction, concentrating the filtrate to an extract, and recovering acetone;

step 2: adding water with a pH of 6±0.1 at room temperature to the extract in proportion with the volume ratio of the extract to the water being 1:7, and resting for crystallization for 24 hours;

step 3: skimming off black oily substance floating on the surface, performing suction filtration to obtain light-green sediment underneath, and drying the sediment;

step 4: heating to dissolve the crude product in pure water with a pH of less than 7 and an amount 18 times that of the crude product, and after thorough dissolution, adding 5% activated carbon for decolorization and impurity removing;

step 5: performing suction filtration, and cooling the mother solution and resting for crystallization;

step 6: after the mother solution being cooled to room temperature, performing suction filtration to obtain crystal, and drying the crystal so as to obtain 25 grams of white powder of dihydromyricetin; and step 7: detecting a content with HPLC.

Embodiment 2

Referring to the FIGURE, the present invention provides an embodiment: a dihydromyricetin extraction and purification process, comprising the following steps:

step 1: weighing a raw material of 1 kg of dry leaves of *Ampelopsis grossedentata* produced in Zhangjiajie, Hunan Province, China, adding an extraction solvent in an amount 5 times that of the raw material to perform reflux extraction at 60° C. for 50 minutes, where the extraction solvent is acetone, after performing three times of extraction and filtering of extraction solutions, combining filtrates from the three times of extraction, concentrating the filtrate to an extract, and recovering acetone;

step 2: adding water with a pH of 6±0.1 at room temperature to the extract in proportion with the volume ratio of the extract to the water being 1:7, and resting for crystallization for 24 hours;

step 3: skimming off black oily substance floating on the surface, performing suction filtration to obtain light-green sediment underneath, and drying the sediment;

step 4: heating to dissolve the crude product in pure water with a pH of less than 7 and an amount of 20 times that of the crude product, and after thorough dissolution, adding 5%-10% activated carbon for decolorization and impurity removing;

step 5: performing suction filtration, and cooling the mother solution and resting for crystallization;

step 6: after the mother solution being cooled to room temperature, performing suction filtration to obtain crystal, and drying the crystal so as to obtain 253 grams of white powder of dihydromyricetin; and step 7: detecting a content with HPLC.

Embodiment 3

Referring to the FIGURE, the present invention provides an embodiment: a dihydromyricetin extraction and purification process, comprising the following steps:

step 1: weighing a raw material of 10 kg of dry leaves of *Ampelopsis grossedentata* produced in Zhangjiajie, Hunan Province, China, adding an extraction solvent in an amount 5 times that of the raw material to perform reflux extraction at 60° C. for 50 minutes, where the extraction solvent is acetone, after performing three times of extraction and filtering of extraction solutions, combining filtrates from the three times of extraction, concentrating the filtrate to an extract, and recovering acetone;

step 2: adding water with a pH of 6±0.1 at room temperature to the extract in proportion with the volume ratio of the extract to the water being 1:7, and resting for crystallization for 24 hours;

step 3: skimming off black oily substance floating on the surface, performing suction filtration to obtain light-green sediment underneath, and drying the sediment;

step 4: heating to dissolve the crude product in pure water with a pH of less than 7 and an amount 19 times that of the crude product, and after thorough dissolution, adding 5% activated carbon for decolorization and impurity removing;

step 5: performing suction filtration, and cooling the mother solution and resting for crystallization;

step 6: after the mother solution being cooled to room temperature or below 15° C., performing suction filtration to obtain crystal, and drying the crystal so as to obtain 2.48 kg of white powder of dihydromyricetin; and step 7: detecting a content with HPLC.

Table 1 presents performance indicators for dihydromyricetin of Embodiments 1, 2, and 3.

TABLE 1

| | Embodiment | | |
|---|---|---|---|
| Items | Embodiment 1 | Embodiment 2 | Embodiment 3 |
| Appearance | white powder | white powder | white powder |
| Yield | 25% | 25.3% | 24.8% |
| Content | 99.2% | 99.1% | 99.3% |

TABLE 1-continued

| | Embodiment | | |
|---|---|---|---|
| Items | Embodiment 1 | Embodiment 2 | Embodiment 3 |
| Solvent content | <0.5% | <0.5% | <0.5% |
| Moisture | <1% | <1% | <1% |

The implementations of the present invention have been described in detail above in conjunction with the accompanying drawings, but the present invention is not limited to the foregoing implementations. Within the scope of knowledge of those skilled in the art, various changes can be made without departing from the spirit of the present invention.

What is claimed is:

1. A dihydromyricetin extraction and purification process, comprising the following steps:

step 1: weighing a raw material, adding an extraction solvent in an amount 5 times that of the raw material to perform reflux extraction, after performing three times of extraction and filtering of extraction solutions, combining filtrates from the three times of extraction, concentrating the filtrate to an extract, and recovering acetone;

step 2: adding water to the extract in proportion and resting for crystallization for 24 hours;

step 3: skimming off black oily substance floating on the surface, performing suction filtration to obtain light-green sediment underneath, and drying the sediment;

step 4: heating and dissolving the crude product in pure water, and after thorough dissolution, adding 5%-10% activated carbon for decolorization and impurity removing;

step 5: performing suction filtration, and cooling the mother solution and resting for crystallization;

step 6: after the mother solution being cooled, performing suction filtration to obtain crystal, and drying the crystal so as to obtain white powder of dihydromyricetin; and step 7: detecting a content with HPLC.

2. The dihydromyricetin extraction and purification process according to claim 1, wherein the raw material is dry leaves of *Ampelopsis grossedentata*, produced in Zhangjiajie, Hunan Province, China, with an amount of 0.1 kg to 10 kg.

3. The dihydromyricetin extraction and purification process according to claim 1, wherein the extraction solvent is acetone.

4. The dihydromyricetin extraction and purification process according to claim 1, wherein a temperature for the reflux extraction in step 1 is 60° C. and an extraction time is 50 minutes.

5. The dihydromyricetin extraction and purification process according to claim 1, wherein the water in step 2 has a pH of 6±0.1 at room temperature.

6. The dihydromyricetin extraction and purification process according to claim 1, wherein a volume ratio of the extract to the water in step 2 is 1:7.

7. The dihydromyricetin extraction and purification process according to claim 1, wherein the pure water in step 4 has a pH of less than 7.

8. The dihydromyricetin extraction and purification process according to claim 1, wherein the amount of the pure water used in step 4 is 18-20 times that of the crude product.

9. The dihydromyricetin extraction and purification process according to claim 1, wherein the mother solution in step 6 is cooled to room temperature or below 15° C.

* * * * *